(12) United States Patent
Heider et al.

(10) Patent No.: US 7,385,068 B2
(45) Date of Patent: Jun. 10, 2008

(54) STEARATE COMPOSITION AND METHOD

(75) Inventors: Todd P. Heider, Imperial, MO (US); Steven M. Wolfgang, Reston, VA (US); Scot R. Randle, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 232 days.

(21) Appl. No.: 11/154,849

(22) Filed: Jun. 16, 2005

(65) Prior Publication Data

US 2006/0281937 A1 Dec. 14, 2006

Related U.S. Application Data

(63) Continuation-in-part of application No. PCT/US2004/024485, filed on Jul. 28, 2004.

(60) Provisional application No. 60/490,596, filed on Jul. 28, 2003.

(51) Int. Cl.
*C07C 247/00* (2006.01)
*C07C 51/00* (2006.01)
*C07C 51/43* (2006.01)

(52) U.S. Cl. ............... 552/1; 554/156; 554/195; 554/200; 554/211

(58) Field of Classification Search ........ 554/211, 554/195, 200
See application file for complete search history.

(56) References Cited

U.S. PATENT DOCUMENTS

| | | | |
|---|---|---|---|
| 2,313,844 A | 3/1943 | Sullivan | |
| 2,417,071 A | 3/1947 | Gebhart et al. | |
| 2,628,202 A | 2/1953 | Allison et al. | |
| 2,650,932 A | 9/1953 | Kebrich et al. | |
| 2,857,313 A | 10/1958 | Cooper et al. | |
| 2,862,014 A | 11/1958 | Rue | |
| 2,945,051 A | 7/1960 | Davis | |
| 3,803,188 A | 4/1974 | Scott et al. | |
| 3,876,551 A | 4/1975 | Laufer et al. | |
| 3,997,692 A | 12/1976 | Lamberti | |
| 4,060,535 A | 11/1977 | Cinco | |
| 4,145,542 A | 3/1979 | Nakagawa et al. | |
| 4,235,794 A * | 11/1980 | Rieber et al. ............ | 554/73 |
| 4,294,771 A | 10/1981 | Pietralla et al. | |
| 4,307,027 A | 12/1981 | Borzelli et al. | |
| 4,435,857 A | 3/1984 | Meloy | |
| 4,731,195 A | 3/1988 | Olson | |
| 4,777,080 A | 10/1988 | Harris, Jr. et al. | |
| 4,800,082 A | 1/1989 | Karbowski et al. | |
| 4,927,548 A | 5/1990 | Hirsch et al. | |
| 5,028,486 A | 7/1991 | Dunski | |
| 5,032,632 A | 7/1991 | Saxton | |
| 5,100,675 A | 3/1992 | Cho et al. | |
| 5,175,322 A | 12/1992 | Yoshizawa et al. | |
| 5,277,832 A | 1/1994 | Gill et al. | |
| 5,364,610 A | 11/1994 | Merris, Jr. | |
| 5,434,277 A * | 7/1995 | Hwu et al. ............ | 554/71 |
| 5,447,729 A | 9/1995 | Belenduik et al. | |
| 5,631,215 A | 5/1997 | Kinsman | |
| 5,681,980 A | 10/1997 | Beerse et al. | |
| 5,897,876 A | 4/1999 | Rudnic et al. | |
| 5,900,399 A | 5/1999 | Seiter et al. | |
| 5,952,004 A | 9/1999 | Rudnic et al. | |
| 5,997,768 A | 12/1999 | Scully, Jr. | |
| 6,395,701 B1 | 5/2002 | Connor et al. | |
| 6,437,000 B1 | 8/2002 | Mulye | |
| 6,699,403 B2 | 3/2004 | Dluzneski et al. | |
| 2002/0052411 A1 | 5/2002 | Gobel et al. | |
| 2002/0076436 A1 | 6/2002 | Batra et al. | |
| 2002/0187536 A1 | 12/2002 | Kulkami et al. | |
| 2003/0166628 A1 | 9/2003 | Doyle et al. | |
| 2003/0185903 A1 | 10/2003 | Cole et al. | |
| 2004/0092418 A1 | 5/2004 | Connor et al. | |
| 2004/0092419 A1 | 5/2004 | Connor et al. | |
| 2004/0124397 A1 | 7/2004 | Dluzneski et al. | |
| 2004/0171161 A1 | 9/2004 | Miller | |
| 2004/0242908 A1 | 12/2004 | Jennings et al. | |
| 2005/0009897 A1 | 1/2005 | Anderson et al. | |
| 2005/0042284 A1 | 2/2005 | Hobden et al. | |
| 2006/0247456 A1 * | 11/2006 | Wolfgang et al. ............ | 554/195 |

FOREIGN PATENT DOCUMENTS

| WO | WO 01/05430 A1 | 1/2001 |
|---|---|---|
| WO | WO 03/011214 A2 | 2/2003 |

OTHER PUBLICATIONS

Sigma-Aldrich Catalogue 2001 Milwaukee p1034.*
Keith David the Chemical, Physical, and Lubricative Properties of Magnesium StearateUniv of Wisconsin vol. 48/03-B of Dissertation Abstracts International.*
Steffens et al.; "The Magnesium Stearate Problem"; Publication; Dec. 1993; pp. 16, 17 and 19; Manufacturing Chemist.
Beckers et al.; "Investigation of the Structural Stability of Magnesium Stearate by Temperature and Humidity Controlled X-Ray Diffraction"; http://www.dxcicdd.com/01/pdf/D-036.pdf.
Friedrich et al; "Influence of Magnesium Stearate Crystal Habitus on Lubrication of Tablettose 80-Tablets"; http://www.pharmtech.uni-bonn.de/forschung/zip/friedrichAPV2002.pdf.

(Continued)

*Primary Examiner*—Yvonne Eyler
*Assistant Examiner*—M Louisa Lao

(57) ABSTRACT

An improved alkaline earth metal stearate composition is disclosed and is prepared by reacting a fatty acid component including stearic acid and palmitic acid with an alkali hydroxide to form an alkaline soap. An aqueous metal salt solution is then added to the soap, and pH adjusted to less than about pH 8 to form the improved alkaline earth metal stearate. The improved alkaline earth metal stearate provides a substantially pure amount of the dihydrate form of the stearate.

26 Claims, No Drawings

OTHER PUBLICATIONS

Koivisto et al.; "The Effect of Moisture and Degassing on some Physical Properties of Vegetable Grade Magnesium Stearate Powders"; http://www.physics.utu.fi/industrial/pdf/koivisto1.pdf.

Swaminathan et al.; "An Examination of the Moisture Sorpotion Characteristics of Commercial Magnesium Stearate"; AAPS PharmSci/Tech 2001, 2(4) Article 28; http://www.aapspharmscitech.org/articles/pt0204/pt020428/pt020428.pdf.

* cited by examiner

STEARATE COMPOSITION AND METHOD

REFERENCES TO RELATED APPLICATIONS

This application is a continuation-in-part of PCT/US2004/024485, filed Jul. 28, 2004, which designated the United States and claims priority to U.S. provisional application No. 60/490,596, filed Jul. 28, 2003.

BACKGROUND OF INVENTION

This invention relates to the industrial manufacture of alkaline earth metal stearate compositions useful as industrial lubricants for uses including metal forming and tablet formulation of pharmaceutical preparations. More particularly, this invention relates to a process for preparing magnesium stearate lubricant exhibiting improved properties in lubrication and dissolution of pharmaceutical preparations in tablet form.

Numerous patents disclose the utility of stearates as lubricants or powder flow enhancers. U.S. Pat. Nos. 6,437,000, 5,032,632, 5,952,004, 5,447,729, 4,800,082, 4,777,080 and U.S. Published Application 2002/0052411 provide typical disclosures of such utility.

The use of magnesium stearate as a pharmaceutical tableting lubricant is well known in the art. According to USP/NF (2004), magnesium stearate is described as a substance containing at least 40% stearic acid, 90% as the sum of stearic acid and palmitic acid, and not more than 6.0% water. Magnesium stearate commonly used in pharmaceutical applications is a mixture of magnesium stearate and magnesium palmitate, since sources used to derive magnesium stearate include tallow, palm oil, and soybean oil, all of which are glyceryl esters of $C_{16}$ and $C_{18}$ fatty acids. Moreover, the state of magnesium stearate may be amorphous, or exhibit any of the following crystalline forms—anhydrous, monohydrate, dihydrate, and trihydrate. The USP/NF description of the composition and attributes of magnesium stearate does not account for functionality differences of the various crystalline forms. Further, the water content of up to 6.0% allows for products containing many possible combinations of hydrated forms to meet the requirements in the compendial monograph.

Pharmaceutical manufacturers and researchers have found that of the three polymorphic hydrates (mono-, di- and tri-), the dihydrate form is preferred as it provides superior lubricating properties. It is also known that the content of water and the resulting crystal forms contribute to functionality of magnesium stearate. Magnesium stearate compositions that contain some dihydrate are perceived to have advantages in the formulation and manufacture of solid dosage forms. It has been reported that improvements in disintegration, dissolution, crush strength and extrusion force are related specifically to the presence of dihydrate as opposed to other hydrated forms of magnesium stearate. Dihydrate has been reported to have the best anti-caking properties.

However, the prior art has failed to describe a method to manufacture the dihydrate from a mixed fatty acid composition that typifies commercial sources in terms of its stearic acid/palmitic acid content, nor a method for preparing it. There is no description in the prior art to suggest that commercial fatty acids have the correct composition to obtain pure dihydrate, or even significant amounts of dihydrate. The lack of consistency in commercial fatty acid compositions make controlling the content of dihydrate in the finished product challenging. The dihydrate is not an intermediate substance in the formation of the trihydrate from the anhydrous form when it was exposed to high humidity, and is only crystallized from solution under certain circumstances.

Further, currently available magnesium stearate compositions have the potential to adversely affect pharmacological activity by providing a water repellant barrier to dissolution of drugs, and can have a major influence on bioavailability, particularly of sustained release drugs.

In order for the pharmaceutical industry to gauge the potential benefits of the dihydrate form for the purpose of creating new formulations based on these findings, pure or at least well-defined compositions containing dihydrate material must ultimately become commercially available.

Commercially available magnesium stearate is actually a mixture of magnesium stearate and palmitate, and the hydration and degree of crystallinity vary significantly depending upon the manufacturing process, as well as from batch to batch depending on the starting materials. While high-purity forms of magnesium stearate dihydrate or magnesium palmitate dihydrate have been prepared and characterized in the laboratory, there are no commercially viable methods available for the preparation of the preferred dihydrate form.

Improvements and efficiencies in the industrial preparation of stearate salts have been the subject of considerable research. As the number and use of medications, particularly in tablet form, expands, so to does the demand for ingredients employed in pharmaceutical tablet formation as well as in industrial operations. One such industrial application is metalworking that has also increased demand for reasonable priced lubricants of the stearate class, as is found in U.S. Pat. No. 5,277,832.

Another attempt to gain efficiency and an improved product is disclosed in U.S. Pat. No. 5,175,322. This patent discloses a continuous process for manufacturing alkaline earth metal stearate soaps by the double decomposition method wherein a stream of an alkaline earth metal soap and an inorganic metal salt is dropped on a moving impeller of a mixer thereby instantaneously mixing the reactant together followed by rapid discharge from the reactor of the newly formed stearate salt. This process is purported to provide a product free of unreacted starting materials and unwanted by-products. An improved double decomposition reaction was disclosed in U.S. Pat. No. 5,434,277 wherein it is disclosed that such reactions do not provide high purity products because of the presence of unreacted starting materials present in the product. The solution to this problem according to this disclosure is to provide alternated basification-acidification of the reaction mixture. The effectiveness of the alternate treatment of the reaction mixture was shown by DSC analysis of the product indicating the disappearance of stearic acid starting material after alternative treatment. None of the prior disclosures mention the relevance of stearic acid/palmitic acid composition impacting hydration nor any means to control hydration of precipitated stearates in aqueous media.

A publication entitled "The Magnesium Stearate Problem" originally presented as a paper in 1992 and then published in Manufacturing Chemist, December 1993 discloses a study of the variations in lubricant properties of products from various industrial batches of stearate that has been observed in the industry. The observed variations were reported by K. J. Steffens and J. Koglin in an attempt to determine the unexplained cause of performance variation of industrial production batches of stearate salt that seemed identical based on the manufacturers reported attributes.

Significant variations were observed among the commercial sources with respect to lubrication and tablet properties.

The writers classified commercial grades of magnesium stearate into six types distinguished by differences in their hydration and crystallinity. It was determined that crystalline magnesium stearate containing "predominately dihydrate form" was clearly superior when used as lubricant in a model formulation. Unfortunately, no method of manufacturing the pure dihydrate phase has been described in the literature, with the exception of synthesis from relatively pure stearic acid, which is cost prohibitive.

It is therefore desirable to provide an alkaline earth metal stearate composition and related method of production that result in consistent production of the dihydrate form of the alkaline earth metal stearate.

SUMMARY OF INVENTION

An aspect of the present invention is to provide an improved alkaline earth metal stearate composition comprised of the reaction product of at least one fatty acid in a basic solution with at least one alkaline earth metal sulfate. The fatty acid is comprised of at least about 80% by weight stearic acid and at least about 5% by weight palmitic acid.

Another aspect of the present invention is to provide a method for preparing the improved alkaline earth metal stearate composition. At least one fatty acid comprised of at least about 80% by weight stearic acid and at least about 5% by weight palmitic acid is added to a basic aqueous solution. At least one alkaline earth metal sulfate is added, and the at least one alkaline earth metal sulfate reacts with the at least one fatty acid to form the improved alkaline earth metal stearate composition.

In yet another aspect of the present invention there is provided an improved alkaline earth metal stearate composition comprised of at least about 40% alkaline earth metal stearate dihydrate.

In yet a further aspect of the present invention there is provided a method for preparing an alkaline earth metal stearate composition. The method comprises providing a basic aqueous solution and incorporating at least one fatty acid into the basic aqueous solution. The fatty acid is comprised of stearic acid and palmitic acid. At least one alkaline earth metal sulfate is added to form a slurry, and the slurry pH is adjusted to less than about pH 8. The slurry is then subjected to solid-liquid separation via vacuum filtration and resulting wet cake is flash dried to form the improved alkaline earth metal stearate composition.

DETAILED DESCRIPTION OF THE INVENTION

There is provided an improved alkaline earth metal stearate composition and related method of preparation, wherein a substantial portion of the stearate is in the dihydrate form. Methods of making metallic salts of fatty acids are well known in the art. The "double decomposition" method involves a two-step process. First, the fatty acid is reacted with at least one base in a basic aqueous solution, typically at least one alkali hydroxide to form an alkaline soap. Second, at least one aqueous metallic salt solution is added to the soap to form metallic salts of the corresponding fatty acid.

Conventional pharmaceutical preparation of alkaline earth metal stearates, for example magnesium stearate and calcium stearate, typically utilize this method. The stearic acid reacts with an alkali hydroxide, for example NaOH, to form the sodium soap, which then reacts with an alkaline earth metal salt, for example magnesium chloride, as shown below:

  (1)

  (2)

  (3)

Stearate compositions produced by this method exhibit great variation in quality and properties. It is known that commercially available stearic acid typically contains palmitic acid also. While pure stearic acid does have limited availability, the purification is not feasible on an industrial scale.

It has now been determined, however, that this impurity (palmitic acid) can lead to the formation of an improved stearate composition. By manipulating the components of the stearic acid starting material, more specifically the ratio of stearic acid to palmitic acid, a significant amount of the dihydrate form of the stearate product can be formed. The dihydrate form of the stearate provides a product which is substantially crystalline, with substantial platelet formation. The dihydrate form is thought to be responsible for the improved lubricating properties and decreased interference with bioavailability observed with the stearate dihydrate when compared with stearates of similar properties excepting for their hydration.

In the present invention it has been determined that a fatty acid component of at least about 80% by weight stearic acid and at least about 5% by weight palmitic acid, with 88% by weight stearic acid to about 10% by weight palmitic acid being preferred; 90% by weight stearic acid to 8% by weight palmitic acid being more preferred; and about 93% by weight stearic acid to about 5% by weight palmitic acid being optimal.

In an alternative embodiment, in addition to using preferred compositions of stearic/palmitic acids, the water content of the stearic/palmitic acids is defined. In this embodiment, the composition disclosed is comprised of magnesium stearate palmitate dihydrate having a stearate/palmitate ratio of at least 10:1 and a total water content of less than about 6%. Of that 6% water, preferably 15-100% of the total water content is crystalline water dihydrate, with less than about 10% of the total water content being free water, and the remainder of the water content being monohydrate. The fatty acid used in this alternative embodiment contains the sum of stearate and palmitate no less than 98% of the total acid content. The water content and hydration state of the final product vary as the ratio of stearic acid/palmitic acid, pH and conditions of drying are varied. The desired dihydrate is most likely to form in alkaline solution when the ratio of stearic acid/palmitic acid is >10, or at a lesser ratio when the pH is closer to neutral and when the drying temperature does not exceed 60° C.

The composition disclosed in this alternative embodiment exhibits beneficial functionalities including improving powder flow characteristics, reducing ejection force/compression force ratio, and minimizing any retardation of disintegration and dissolution rates of hydrophobic, or poorly water soluble drugs such as dilantin, modafinil, zolpidem and alike, which are frequently observed when conventional magnesium stearate was used as the lubricant in making the tablets.

According to these first two embodiments of the present invention, the fatty acid component is dispersed into a basic aqueous solution, whereby the fatty acid component reacts with the base to form a soap. Optionally, the basic aqueous solution may be heated prior to incorporating the fatty acid component to help to prevent the fatty acid component from congealing. The alkaline earth metal salt, typically magnesium sulfate or calcium sulfate, is then added and the pH is adjusted to provide an alkaline environment to raise the assay of the product by precipitation of any excess Mg as MgO.

In yet another alternative embodiment, a substantially pure magnesium stearate dihydrate is attained by controlling the pH during the precipitation step. As is outlined above, the conventional method for producing magnesium stearate comprises the reaction of stearic acid with an alkali hydroxide to form a metal soap, which then reacts with an alkaline earth metal salt to form the magnesium stearate. In the conventional reaction, the formation of the hydrated magnesium soaps is a consequence of the aqueous precipitation medium. The most common hydrated form obtained when the resulting solution is alkaline is the monohydrate form.

It has been determined that if the pH of the precipitation medium is less alkaline, or when the solution is adjusted to a pH of less than about 8, either during or after precipitation, there is a greater tendency to obtain the hydrated form, magnesium stearate dihydrate. In this embodiment, the fatty acid starting material can be any combination of stearic and palmitic acid totaling at least 90%. This allows the production of the dihydrate form from any commercially available fatty acid mixtures, which are typically only about 40% stearic acid, with at least about 90% total stearic and palmitic acid.

The fatty acid is reacted with sodium hydroxide in water at a temperature of about 75° C., forming a soluble sodium stearate/sodium palmitate mixture which is be referred to as "soap solution." The fatty acid and sodium hydroxide are reacted at an approximately 1:1 molar ratio and sodium hydroxide added to produce a soap solution which is slightly alkaline. Any combination of stearic and palmitic acids can be used to form the relatively pure dihydrate form of magnesium stearate.

$$C_{17}H_{35}COOH + NaOH \rightarrow C_{17}H_{35}COONa + H_2O \quad (4)$$

An aqueous alkaline earth metal sulfate solution is then added to the soap solution, whereby insoluble alkaline earth metal stearate is precipitated. The non-limiting illustrative reaction equation below utilizes magnesium sulfate as the alkaline earth metal sulfate.

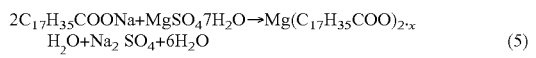

$$2C_{17}H_{35}COONa + MgSO_4 7H_2O \rightarrow Mg(C_{17}H_{35}COO)_2 \cdot xH_2O + Na_2SO_4 + 6H_2O \quad (5)$$

The alkaline earth metal sulfate is added in slight excess to ensure that all sodium stearate reacts to form the alkaline earth metal stearate. The pH after this step is typically about 6.0-6.7. It is noted that the soap solution may be produced by any conventional method, as are well known in the art.

The soluble salts are removed from the product by adding water to the slurry, mixing and then separating and draining off the water. The pH after this step is typically about 8.0-8.5.

The pH of the alkaline earth metal stearate slurry is then adjusted with an acid. Suitable acids include but are not limited to inorganic acids such as sulfuric acid, hydrochloric acid, nitric acid and mixtures thereof. The pH is preferably adjusted to below about pH 8; with a pH of below 7 being more preferred; and a pH of about 6.3 to about 6.4 being most preferred, although significant formation of the dihydrate form has been accomplished at lower pH, for example at pH 5. The pH may be adjusted before or after the precipitation of the stearate. In an illustrative embodiment, the pH adjustment is made immediately before feeding to the flash drying system.

In an illustrative example utilizing magnesium sulfate, wet cakes formed at pH of 6.3-6.4 were substantially pure magnesium stearate dihydrate, at least about 95% or better, with no other hydrated forms present, as analyzed using Thermogravimetric Analysis. In one embodiment, the liquid or slurry remaining after wet cake formation is recovered for use as a component in the basic aqueous solution of subsequent dihydrate formation.

There was also a significant amount of dihydrate present when the pH was adjusted to 8.0 before drying. The dihydrate was approximately 70% with the remainder being monohydrate form.

It is believed that significant amounts of dihydrate are formed when the pH of the aqueous magnesium stearate slurry is lower than 8.5 before drying. At a pH above 8.5, the amount of dihydrate decreases rapidly until there is no dihydrate formed when the pH of the aqueous magnesium stearate slurry is adjusted to a pH of 9.0 or higher.

The magnesium stearate is typically flash dried at about 50° C. to about 90° C. with about 60° C. to about 65° C. being preferred. The product tends to dehydrate slightly upon drying, but still contains greater than about 80% dihydrate form with the remainder being the anhydrous crystal of the dihydrate. An illustrative drying system consists of a rotary vacuum filter (solid-liquid separation), hammer mill, natural gas fueled furnace, and a pneumatic conveying system, although the product may be dried and processed by any conventional method. Other suitable types of drying include spray drying, tray drying, and fluid bed drying at the 50-90° C. range to retain the dihydrate that was formed during pH adjustment of the magnesium stearate slurry.

The following examples are given for illustrative purposes only and are not intended to limit the scope of the present invention in any way.

EXAMPLES

Example 1

A magnesium stearate composition containing a variable ratio of discrete monohydrate and dihydrate polymorphs is manufactured from a "soap solution" via precipitation, as is well known in the art. The salt of this illustrative example is formed by mixing of at least one fatty acid and at least one strong base, NaOH and a magnesium salt, MgSO$_4$. In the present invention, the soap solution is produced from a fatty acid mixture of suitable stearic/palmitic acid composition to obtain an appreciable amount of the dihydrate form of the resulting stearate. Addition of the alkaline earth metal salt to an alkaline "soap solution" results in the precipitation of magnesium stearate containing the dihydrate phase. The precipitate is separated from the liquor, and dried to a water content of 3.5-6.0%, predominately water of hydration. A fine-particulate solid is obtained. The product is designed for use as a pharmaceutical lubricant/mold release agent, but can be used for other applications, as is known in the art.

The following is an illustrative example of an industrial manufacturing process for a product containing the desired magnesium stearate dihydrate and is not intended to limit the present invention to the production of magnesium stearate/palmitate for pharmaceutical uses:

An aqueous solution, either water or a heel from a previous batch was heated to a temperature at which the fatty acid did not congeal when introduced to the aqueous solution, as is well known. A 50% sodium hydroxide solution was added in at least a 1:1 molar ratio to the fatty acid, so that substantially all the fatty acid constituents were converted to the sodium soap. The fatty acid component was then added until the solution was slightly alkaline to phenolphthalein indicator. In this illustrative example, a fatty acid composition of about 93% by weight stearic acid to about 5% by weight palmitic acid was used.

A solution of magnesium sulfate was then added, without agitation, in an amount to substantially precipitate the sodium soap, thereby forming the magnesium stearate/palmitate. The reaction mixture was then mixed to create a homogeneous mixture and insure reaction with the magnesium sulfate, typically about 20 minutes. The reaction mixture remained heated throughout this and the remaining steps to prevent any solidification of the reaction mixture, thereby providing ease of handling. The pH was then adjusted with sodium hydroxide to precipitate any excess magnesium as MgO. An illustrative pH range is from about 9.0 to about 9.5. A solid-liquid separation was performed, and the resulting solid product was dried, and deagglomerated by suitable conventional methods. These steps and reaction conditions are well known to those skilled in the art.

This resulting product was characterized as containing a mixture of magnesium stearate and magnesium palmitate as mixed hydrates as follows:

1. The product had a loss on drying of 3.5-6.0% indicating a significant amount of the dihydrate form is present. TGA indicates 2 water loss events, one at about 60° C. and one at about 90° C., corresponding to the dihydrate and monohydrate forms respectively.

2. DSC analysis showed 2 endothermic transitions between 100°-135° C. (ca. 118° C. and 128° C. for Mg stearate) as a result of 2 pseudopolymorphs that are each derived from unique hydrates.

3. X-ray diffraction showed crystallinity (not amorphous), and exhibited a characteristic XRD pattern indicating the dihydrate form is present.

The product had regular or irregular (e.g. fragmented) platelet morphology. Other features of the manufacturing process that are considered relevant to the manufacture of magnesium stearate are obvious to those skilled in the art.

Example 2

A magnesium stearate composition is prepared according to the method of Example 1 utilizing fatty acid having a stearic/palmitic acid ratio of at least about 10:1 and a total water content of less than about 6%. Of that 6% water, preferably 15-100% of the total water content is crystalline water dihydrate, with less than about 10% of the total water content being free water, and the remainder of the water content being monohydrate. The fatty acid used in this alternative embodiment contains the sum of stearate and palmitate no less than 98% of the total acid content. The pH adjustment is made to render the reaction mixture substantially neutral. The product is dried at a temperature at or below 60° C. to remove most of the bulk water resulting in a fine, crystalline powder containing the dihydrate phase as evidenced by TGA/DSC.

Example 3

A magnesium sulfate solution is prepared by dissolving 98 grams of magnesium sulfate heptahydrate in 643 mL of water. The mixture is stirred at 80° C. until the salt is dissolved. In a separate vessel add 34 mL of 50% (w/w) NaOH to 1.13 liters of water and heat to 90° C. An alkaline sodium stearate (soap) is made by adding 181 grams of fatty acid containing 93% stearic acid and 5% palmitic acid to the NaOH solution maintaining the temperature at 90° C. while stirring. 681 mL of water is added to the soap solution, lowering its temperature to 75° C. The magnesium sulfate solution is added to the soap solution and stirred to assure complete reaction. Once the precipitation is complete the batch is adjusted to a pH of 9.0 using 50% NaOH. The resulting solids are washed with water to remove sodium sulfate byproduct. The solids are dried at 60° C. The product contains a combination of the monohydrate and dihydrate forms of magnesium stearate palmitate.

Example 4

A soap solution was formed by reacting a fatty acid (a mixture of about 65% Stearic and about 35% Palmitic and small percentage of other fatty acids) (181 g) with sodium hydroxide in water (34 ml of 50% wt/wt NaOH added to 1.13 liters of water) at 90° C., forming a soluble sodium stearate soap solution. The resulting soap solution is slightly alkaline so that 5 mL of the slurry dissolved in acetone solution, water and phenolphthalein indicator requires 0.1-0.3 mL of 0.1 N HCl to titrate to the endpoint. Aqueous magnesium sulfate solution was prepared by dissolving 98 grams of magnesium sulfate heptahydrate in 643 mL of water. The magnesium sulfate solution was added to the soap solution and 191 g insoluble magnesium stearate (weight as the monohydrate) was precipitated. The magnesium sulfate was added in slight excess to ensure that all sodium stearate reacts to form magnesium stearate. The pH after this step was 6.2-6.8. The pH was adjusted to a range of 9.0 to 9.5 by adding 50% wt/wt NaOH in water. The soluble salts were removed by washing the product with city water (3400 ml.) The pH after this step was 8.5. Immediately before feeding the magnesium stearate slurry into a flash drying system, the pH of the slurry was adjusted by adding sulfuric acid until a pH of 6.3 was attained. The resulting wet cakes formed at pH of 6.3 were substantially pure magnesium stearate dihydrate, greater than 90% purity, with no other hydrated forms present when analyzed using thermogravimetric analysis. The magnesium stearate was flash dried at a target temperature of 71° C., resulting in slight dehydration of the product, but greater than 80% dihydrate form with the remainder being the anhydrous crystal of the dihydrate. The drying system consisted of a rotary vacuum filter (solid-liquid separation), hammer mill, natural gas fueled furnace, and a pneumatic conveying system. The flash drying system has a residence time of less than 30 seconds and a typical inlet temperature of 150° C. to 260° C. The hammer mill contains 12 hammers and rotates at 1800 rpm and acts mainly to deagglomerate the wet cake to facilitate drying.

Example 5

A magnesium stearate composition was made according to Example 4, adjusting the pH to 5.0. The resulting composition was greater than 90% magnesium stearate dihydrate, with no other hydrated forms present when analyzed using thermogravimetric analysis.

Example 6

Three magnesium stearate compositions were made according to Example 4, adjusting the pH to 6.3, 7.3 and 8.0.

The resulting compositions were characterized via x-ray powder diffraction using a Siemens D500 X-ray Diffractometer utilizing a Long Fine Focus X-ray Tube (Type: FL Cu 4KE) and a diffracted beam monochromator mounted in front of a scintillation detector. The instrument was interfaced with an IBM-compatible computer for data acquisition and analysis using Materials Data, Inc. software including DataScan and Jade. Each sample was uniformly crushed (not ground) with a spatula edge, and dispersed on a quartz, zero-background holder.

Experimental Parameters:
Scan range—2.0 to 40.0 deg 2-theta
Display range—2.0 to 40.0 deg 2-theta
Step size—0.02 deg 2-theta
Scan time per step—1.0 seconds
Radiation source—copper Kα (1.5406 Å)
X-ray tube power—40 kV/30 mA The pattern obtained for the composition adjusted to pH 6.3 was consistent with substantially pure dihydrate form.

The pattern obtained for the compositions adjusted to pH 7.3 and 8.0 were consistent with a mixture of monohydrate, dihydrate and trihydrate phases.

Having described the invention in detail, those skilled in the art will appreciate that modifications may be made of the invention without departing from its' spirit and scope. Therefore, it is not intended that the scope of the invention be limited to the specific embodiments described. Rather, it is intended that the appended claims and their equivalents determine the scope of the invention.

The invention claimed is:

1. An alkaline earth metal stearate composition comprising alkaline earth metal stearate monohydrate and alkaline earth metal stearate dihydrate, the composition comprised of at least 40% earth metal stearate dihydrate and at least 5% palmitic acid, wherein the alkaline earth metal is selected from the group consisting magnesium and calcium.

2. The composition of claim 1 wherein the alkaline earth metal stearate composition is comprised of at least 70% alkaline earth metal stearate dihydrate.

3. The composition of claim 1 wherein the alkaline earth metal stearate composition is comprised of at least 99% alkaline earth metal stearate dihydrate.

4. A magnesium stearate composition comprising magnesium stearate monohydrate and magnesium stearate dihydrate and at least 5% palmitic acid, the composition comprised of at least 40% magnesium stearate dihydrate.

5. The composition of claim 4 wherein the magnesium stearate composition is comprised of at least 70% magnesium stearate dihydrate.

6. The composition of claim 4 wherein the magnesium stearate composition is comprised of at least 99% magnesium stearate dihydrate.

7. A method for preparing an alkaline earth metal stearate composition comprising alkaline earth metal stearate monohydrate and alkaline earth metal stearate dihydrate, the method comprising: providing a basic aqueous solution; incorporating at least one fatty acid, the fatty acid including at least 90% total stearic acid and palmitic acid, into the basic aqueous solution; adding at least one alkaline earth metal sulfate, whereby the alkaline earth metal stearate precipitates to form a slurry of the alkaline earth metal stearate composition; and adjusting the pH of the slurry to less than about pH 8 wherein the alkaline earth metal is selected from the group consisting of magnesium and calcium.

8. The method of claim 7 wherein the basic aqueous solution comprises water and NaOH.

9. The method of claim 7 wherein the pH of the slurry is adjusted to less than about pH 7.

10. The method of claim 7 wherein the pH of the slurry is adjusted to a pH of about 6.3 to a pH of about 6.4.

11. The method of claim 7 wherein the pH of the slurry is adjusted to a pH of about 5.0.

12. The method of claim 7 wherein the pH of the slurry is adjusted with an organic acid selected from the group consisting of sulfuric acid, hydrochloric acid, nitric acid and mixtures thereof.

13. The method of claim 7 wherein the pH of the slurry is adjusted as the alkaline earth metal stearate precipitates.

14. The method of claim 7 wherein the pH of the slurry is adjusted after the alkaline earth metal stearate precipitates.

15. The method of claim 7 further comprising performing a liquid-solid separation to remove the alkaline earth metal stearate composition from the slurry.

16. The method of claim 15 further comprising recovering the slurry for use in a subsequent preparation of alkaline earth metal stearate composition, wherein the recovered slurry is added to the basic aqueous solution.

17. A method for preparing a magnesium stearate composition comprising magnesium stearate monohydrate and magnesium stearate dihydrate, the method comprising: providing a basic aqueous solution; heating the basic aqueous solution; incorporating at least one fatty acid, the fatty acid including at least 90% total stearic acid and palmitic acid, into the basic aqueous solution, continuing heating the basic aqueous solution and the at least one fatty acid until the at least one fatty acid is dispersed within the basic aqueous solution; adding a solution of magnesium sulfate, whereby the magnesium sulfate reacts with the at least one fatty acid to form a slurry the magnesium stearate composition; and adjusting the pH of the slurry to less than a pH of about 8.

18. The method of claim 17 wherein the basic aqueous solution comprises water and NaOH.

19. The method of claim 17 wherein the pH is adjusted with an organic acid selected from the group consisting of sulfuric acid, hydrochloric acid, nitric acid and mixtures thereof.

20. The method of claim 17 wherein the pH of the slurry is adjusted to less than about 7.

21. The method of claim 17 wherein the pH of the slurry is adjusted to a pH of about 6.3 to about 6.4.

22. The method of claim 17 wherein the pH of the slurry is adjusted to a pH of about 5.0.

23. The method of claim 17 wherein the pH of the slurry is adjusted as the magnesium stearate composition precipitates.

24. The method of claim 17 wherein the pH of the slurry is adjusted after the magnesium stearate composition precipitates.

25. The method of claim 17 further comprising performing a liquid solid separation to recover the magnesium stearate composition from the slurry.

26. The method of claim 25 further comprising recovering the slurry for use in a subsequent preparation of alkaline earth metal stearate composition, wherein the recovered slurry is added to the basic aqueous solution.

* * * * *